(12) United States Patent
Obae et al.

(10) Patent No.: US 9,592,199 B2
(45) Date of Patent: *Mar. 14, 2017

(54) CELLULOSE POWDER

(71) Applicant: ASAHI KASEI CHEMICALS CORPORATION, Tokyo (JP)

(72) Inventors: Kazuhiro Obae, Tokyo (JP); Masayuki Kakizawa, Tokyo (JP); Mitsuo Yamashita, Tokyo (JP); Shinji Matsui, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/403,297

(22) PCT Filed: May 30, 2013

(86) PCT No.: PCT/JP2013/065113
§ 371 (c)(1),
(2) Date: Nov. 24, 2014

(87) PCT Pub. No.: WO2013/180248
PCT Pub. Date: Dec. 5, 2013

(65) Prior Publication Data
US 2015/0150804 A1    Jun. 4, 2015

(30) Foreign Application Priority Data

May 31, 2012  (JP) ................................ 2012-124494

(51) Int. Cl.
| | | |
|---|---|---|
| *C08L 1/02* | (2006.01) | |
| *C08J 3/12* | (2006.01) | |
| *A61K 9/14* | (2006.01) | |
| *A61K 47/38* | (2006.01) | |
| *B01D 1/18* | (2006.01) | |
| *F26B 5/00* | (2006.01) | |
| *A61K 9/16* | (2006.01) | |
| *A61K 9/20* | (2006.01) | |

(52) U.S. Cl.
CPC .............. *A61K 9/146* (2013.01); *A61K 47/38* (2013.01); *B01D 1/18* (2013.01); *C08J 3/122* (2013.01); *C08L 1/02* (2013.01); *F26B 5/00* (2013.01); *A61K 9/1652* (2013.01); *A61K 9/2054* (2013.01); *C08J 2301/04* (2013.01); *Y10T 428/2982* (2015.01)

(58) Field of Classification Search
CPC ......... C08L 1/02; A61K 47/38; A61K 9/2054; Y10T 428/2982
See application file for complete search history.

(56) References Cited

U.S. PATENT DOCUMENTS

| | | |
|---|---|---|
| 4,159,345 A | 6/1979 | Takeo et al. |
| 2004/0053887 A1 | 3/2004 | Obae et al. |
| 2005/0163868 A1 | 7/2005 | Matsumoto et al. |
| 2007/0028801 A1 | 2/2007 | Yamasaki et al. |
| 2009/0022791 A1 | 1/2009 | Obae et al. |
| 2010/0291161 A1 | 11/2010 | Obae et al. |
| 2012/0045636 A1 | 2/2012 | Obae et al. |
| 2013/0108872 A1 | 5/2013 | Magome et al. |

FOREIGN PATENT DOCUMENTS

| | | |
|---|---|---|
| JP | 40-26274 B | 11/1965 |
| JP | 53-127553 A | 11/1978 |
| JP | S56-2047 B2 | 1/1981 |
| JP | 57-212231 A | 12/1982 |
| JP | 8-104650 A | 4/1996 |
| JP | 2005-232260 A | 9/2005 |
| JP | 2012-1474 A | 1/2012 |
| WO | WO 02/02643 A1 | 1/2002 |
| WO | 2004/006945 A1 | 1/2004 |
| WO | 2004/106416 A | 12/2004 |
| WO | WO 2006/115198 A1 | 11/2006 |
| WO | 2009/157564 A1 | 12/2009 |
| WO | WO 2012/002253 A1 | 1/2012 |

OTHER PUBLICATIONS

Nippon paper chemical Co., Ltd. catalog of KC Flock published on May 3, 2006.
Nippon paper chemical Co., Ltd. catalog of KC Flock published on Apr. 30, 2010.
Experimental report of the third party issued with respect to application No. 2014-518743, mail date is Jul. 7, 2015.
International Search Report issued with respect to application No. PCT/JP2013/065113, mail date is Jul. 9, 2013.
IPER and Written Opinion from PCT/JP2013/065113, mailed Dec. 2, 2014.

*Primary Examiner* — Gina Justice
(74) *Attorney, Agent, or Firm* — Greenblum and Bernstein, P.L.C.

(57) ABSTRACT

This cellulose powder has: an average degree of polymerization of 100 to 350; a weight average particle size of over 30 μm, but less than 250 μm; an apparent specific volume of 2 to less than 15 cm³/g; and a particle size distribution sharpness of 1.5 to 2.9.

14 Claims, 2 Drawing Sheets

CELLULOSE POWDER

TECHNICAL FIELD

The present invention relates to cellulose powders used in pharmaceutical, food, and industrial applications. More specifically, the present invention relates to cellulose suitable for excipients for granulation during granulation of Kampo medicines, sticky ingredients, and the like in applications of pharmaceuticals, and molded articles comprising the cellulose.

BACKGROUND ART

Kampo medicines, which are bulky and compounded in large amounts, increase the sizes of tablets prepared by a direct compression tableting method. Such large sizes of the tablets lead to difficulties in administration thereof. For this reason, a wet granulation method is used in preparation of tablets containing Kampo medicines. At this time, extract powders or the like, when compounded, exhibit stickiness or moisture absorbing properties, causing low granulation yield, broad particle size distribution, poor fluidity of the resulting granules, a large variation in the weight of tablet in pressing, and the like. In addition, sticky ingredients delay disintegration of the tablets. To solve these problems, a method of compounding a microcrystalline cellulose is known.

Patent Literature 1 discloses use of a microcrystalline cellulose that can improve compactibility and disintegration properties in preparation by a direct compression tableting method.

Patent Literature 2 discloses a tablet including a microcrystalline cellulose and an inorganic compound, and prepared by direct compression tableting of the microcrystalline cellulose and the inorganic compound.

Besides, Patent Literatures 3 to 6 disclose cellulose powders, which are known as excipients which enhance compactibility.

Patent Literature 7 describes compounding of cellulose glycolic acid and sodium hydrogen carbonate during wet granulation that can improve the disintegration properties and dissolution of Kampo extract powders.

CITATION LIST

Patent Literature

Patent Literature 1: JP 8-104650 A
Patent Literature 2: JP 2012-1474 A
Patent Literature 3: JP 40-26274 B
Patent Literature 4: JP 56-2047 B
Patent Literature 5: International Publication No. WO2006/115198
Patent Literature 6: JP 57-212231 A
Patent Literature 7: WO2004/006945

SUMMARY OF INVENTION

Technical Problem

Unfortunately, any conventional cellulose powder which can solve the problems of the wet granulation method has been known.

An object of the present invention is to provide a cellulose powder which attains high compression compatibility, uniformly holds Kampo medicines, sticky ingredients, or the like during granulation thereof, can attain a sharp particle size distribution of the cellulose powder to attain a sharp particle size distribution of the resulting granules, contributes to reduction in the disintegration time, and can give stable disintegration properties over time.

Solution to Problem

The present inventors, who have conducted extensive research in consideration of such circumstances, have found that a cellulose powder having physical properties controlled to fall within specific ranges attains high compression compactibility, uniformly holds Kampo medicines, sticky ingredients, or the like during granulation thereof, can attain a sharp particle size distribution of the cellulose powder to attain a sharp particle size distribution of the resulting granules, can reduce the disintegration time, and can give stable disintegration properties over time, and have achieved the present invention. Namely, the present invention is as follows:

(1) A cellulose powder having an average degree of polymerization of 100 to 350, a weight average particle size of more than 30 μm and 250 μm or less, an apparent specific volume of 2 to less than 15 $cm^3/g$, and a sharpness of particle size distribution of 1.5 to 2.9.
(2) The cellulose powder according to (1), wherein the apparent specific volume is 2 to 6 $cm^3/g$.
(3) The cellulose powder according to (1), wherein the apparent specific volume is 2 $cm^3/g$ or more and less than 4 $cm^3/g$.
(4) The cellulose powder according to (1), wherein an intraparticle pore volume is 0.1 $cm^3/g$ or more and less than 0.265 $cm^3/g$.
(5) The cellulose powder according to (1), wherein an amount of organic carbon derived from residual impurities is more than 0.07 and 0.25% or less, the amount of organic carbon derived from residual impurities being defined by an expression (amount of total organic carbon (%) during extraction with aqueous solution of 1% NaOH)–(amount of total organic carbon (%) during extraction with pure water).
(6) The cellulose powder according to (1), wherein the sharpness of particle size distribution is 1.5 to 2.2 or less.
(7) The cellulose powder according to (1), wherein a moisture retention rate is 180 to 250%.
(8) A molded article, including the cellulose powder according to any one of (1) to (7).
(9) The molded article according to (8), wherein the molded article is a tablet containing one or more active ingredients.
(10) A method of preparing a cellulose powder, including: hydrolyzing a natural cellulose substance at a hydrochloric acid concentration of 0.05 to 0.3% at a hydrolysis temperature of 100 to 150° C. for a hydrolysis time of 40 to 110 minutes to control a volume average particle size of particles in a cellulose dispersion liquid after the hydrolysis to be 70 to 150 μm, and then spray drying the resulting dispersion liquid to prepare a cellulose powder having an average degree of polymerization of 100 to 350, a weight average particle size of the cellulose powder of more than 30 μm and 250 μm or less, an apparent specific volume of 2 to 15 $cm^3/g$, and a sharpness of particle size distribution of 1.5 to 2.9.
(11) A molded article including one or more active ingredients, one or more additives selected from saccharides, sugar alcohols, starches, and disintegrating agents, and a cellulose powder, wherein the molded article has a hardness of 50 to 200 N, a tensile strength of 0.1 to 12 MPa, a friability of 0 to 0.5%, a swelling rate of a diameter of the molded article in acetone of 0 to 3.3% or less, and a disintegration time of 20 minutes or less.

(12) The molded article according to (11), comprising 5 to 90% by weight of a cellulose powder.

(13) The molded article according to (11) or (12), wherein an amount of total organic carbon derived from residual impurities in molded article residues obtained through washing of the molded article with acetone, ethanol, pure water, and ethanol sequentially and extraction is more than 0.07 and 0.25% or less.

(14) The molded article according to (11) or (12), wherein the amount of total organic carbon derived from residual impurities in the cellulose powder obtained through washing of the molded article with acetone, ethanol, pure water, and ethanol sequentially and extraction is more than 0.07 and 0.25% or less.

Advantageous Effects of Invention

The cellulose powder according to the present invention attains high compression compactibility, uniformly holds Kampo medicines, sticky ingredients, or the like during granulation thereof, can attain a sharp particle size distribution of the cellulose powder to attain a sharp particle size distribution of the resulting granules, contributes to reduction in the disintegration time, and has an effect of giving stable disintegration properties over time.

DESCRIPTION OF EMBODIMENTS

The present invention will now be described in more detail. The cellulose powder according to the present invention has an average degree of polymerization of 100 to 350, preferably 150 to 300, more preferably 180 to 250. The average degree of polymerization of 100 or more is preferred because the compactibility is improved, and the average degree of polymerization of 350 or less is preferred because the powder has high fluidity and disintegration properties while fibrous properties are not demonstrated. Namely, an average degree of polymerization of 100 to 350 is preferred because it attains particularly well-balanced compactibility, disintegration properties, and fluidity.

The cellulose powder according to the present invention should have a weight average particle size of more than 30 μm and 250 μm or less. A weight average particle size of more than 30 μm improves handling without increasing adhering and aggregating properties, and attains high fluidity. A weight average particle size of 250 μm or less is preferred because such a size does not separate or segregate the cellulose powder from the active ingredient, and may not reduce the content uniformity of formulations. The weight average particle size is preferably more than 30 μm and 180 μm or less.

The cellulose powder according to the present invention should have an apparent specific volume of 2 to 15 $cm^3/g$. The apparent specific volume is preferably 2 to 13 $cm^3/g$, more preferably 2 to 6 $cm^3/g$, particularly preferably 2 $cm^3/g$ or more and less than 4 $cm^3/g$. An apparent specific volume of 2 $cm^3/g$ or more improves compactibility. The upper limit is at most 15 $cm^3/g$ because an apparent specific volume more than the upper limit restores elasticity due to fibrous properties. The upper limit is preferably 6 $cm^3/g$ or less, more preferably less than 4 $cm^3/g$ because fluidity and disintegration properties are improved. The apparent specific volume is preferably 2.3 to 3.8 $cm^3/g$, particularly preferably 3.0 to 3.8 $cm^3/g$.

The cellulose powder according to the present invention preferably has an apparent tapping density of 0.2 to 0.6 $g/cm^3$. The apparent tapping density is more preferably 0.35 to 0.58 $g/cm^3$, particularly preferably 0.4 to 0.55 $g/cm^3$. When an apparent tapping density is 0.6 $g/cm^3$ or less, compactibility is improved.

The cellulose powder according to the present invention preferably has an angle of repose of 36° or more and less than 44° as an index of fluidity of the powder from the viewpoint of the content uniformity. The angle of repose is more preferably 38° to 42°.

The cellulose powder according to the present invention preferably has an intraparticle pore volume of substantially zero. The value of the intraparticle pore volume determined by the method according to WO2006/115198 is preferably 0.1 $cm^3/g$ or more and less than 0.265 $cm^3/g$. If the particles have substantially no inner pores, a large amount of water does not need to be added during granulation, and the time for drying is unnecessary, which are preferable.

The cellulose powder according to the present invention should have a sharpness of particle size distribution of 1.5 to 2.9. The sharpness thereof is preferably 1.5 to 2.2. At a sharpness closer to 1.0, the cellulose powder is monodispersed, which is preferable. An actual sharpness is at most about 1.5. The cellulose powder having a sharpness of particle size distribution of 2.9 or less is preferred because it can uniformly hold Kampo medicines, sticky substances, and the like. Such a cellulose powder attains a sharp particle size distribution in granules prepared by granulation, and does not increase variation in the weight of the tablet during pressing. The cellulose powder prevents delay of disintegration over time. This is also preferable.

In the present invention, the sharpness of particle size distribution is a value obtained as follows: 10 g of a sample is sieved for 10 minutes with a low tapping sieve shaker (sieve shaker type A manufactured by Heiko Seisakusho, Ltd.) and a JIS standard sieve (Z8801-1987) to measure the particle size distribution of the cellulose powder. From the particle size distribution, the integrated weight 10% particle size ($D_{10}$), the integrated weight 50% particle size ($D_{50}$), and the integrated weight 90% particle size ($D_{90}$) are calculated. From these, the sharpness is calculated by the following expression:

sharpness of particle size distribution=$[(D_{50}/D_{10})+(D_{90}/D_{50})]/2$  [Expression 1]

Examination of cellulose powders having different sharpnesses of particle size distribution showed that as the value of sharpnesses of particle size distribution is smaller, granules during granulation have a lower sharpness of particle size distribution.

In the present invention, the granules have a sharpness of particle size distribution of preferably 1.0 to 3.0. The sharpness is more preferably 1.0 to 2.8. The sharpness is preferably closer to 1.0. A sharpness of 3.0 or less is preferred because the granules prepared by granulation do not have broad particle size distribution, and do not delay disintegration.

The sharpness of particle size distribution of granules is determined as follows: 10 g of a sample is sieved for 10 minutes with a low tapping sieve shaker (sieve shaker type A manufactured by Heiko Seisakusho, Ltd.) and a JIS standard sieve (Z8801-1987) to measure the particle size distribution. From the particle size distribution, the cumulative weight 10% particle size ($D_{10}$), the cumulative weight 50% particle size ($D_{50}$), and the cumulative weight 90% particle size ($D_{90}$) are calculated, and the sharpness of particle size distribution of granules is determined from the following expression:

$$\text{sharpness of particle size distribution of granules} = (D_{50}/D_{10} + D_{90}/D_{50})/2$$

The cellulose powder according to the present invention has an amount of organic carbon derived from impurities remaining in the cellulose raw material of preferably more than 0.07 and 0.25% or less. The amount is preferably more than 0.07 and 0.20%, more preferably 0.09 to 0.15%.

In the present invention, the amount of organic carbon derived from residual impurities is defined by the difference between the amount of total organic carbon (TOC) extracted from the cellulose powder (5 g) with pure water (80 mL) and the amount of TOC extracted from the cellulose powder (5 g) with an aqueous solution of 1% sodium hydroxide (80 mL).

The amount of TOC extracted with the aqueous solution of 1% sodium hydroxide reflects the amounts of an alkali-soluble ingredient and a pure water-soluble ingredient contained in the cellulose powder. From the amount of TOC, the amount of TOC extracted with pure water, namely, the pure water-soluble ingredient is subtracted to determine the amount of the alkali-soluble ingredient in the cellulose powder. The value is correlated with the amount of organic carbon derived from residual impurities.

In the cellulose powder according to the present invention, the amount of organic carbon derived from residual impurities, which is defined in the present invention, is higher than that of the cellulose powder prepared by a conventional method. The organic carbon derived from residual impurities is an ingredient slightly contained in the cellulose powder. Surprisingly, the present inventors have found that a larger amount of organic carbon derived from residual impurities leads to higher compression compactibility. The organic carbon derived from residual impurities, although slightly contained, is present on the surfaces of individual cellulose powder particles to enhance the adhesive force.

If the amount of organic carbon derived from residual impurities is controlled to fall within the range specified in the present invention, compactibility is improved by 10 to 300%. The ingredient slightly contained selectively bonds to a sticky ingredient such as Kampo medicines, and uniformly adheres to cellulose particles during granulation, causing a sharp particle size distribution of the granules. Even when the cellulose particles have the same sharpness of particle size distribution, if the amount of organic carbon derived from residual impurities is within a specific range, the granules can have a sharper particle size distribution. The present inventors also have found that such a sharp particle size distribution of the granules improves the fluidity of the granules to reduce variation in the weight of the tablet during pressing and to significantly improve disintegration properties. The present inventors also have found that the cellulose powder according to the present invention does not delay disintegration over time while the conventional cellulose powder delays disintegration after a storage stability test. This is probably because sticky ingredients bonded together due to heat and humidity during the storage stability test to delay disintegration. In contrast, probably because the cellulose powder according to the present invention contains a proper amount of organic carbon derived from residual impurities and has proper moisture retention properties, movement of sticky ingredients and bonding of sticky ingredients are suppressed. If the amount of organic carbon derived from residual impurities is controlled to fall within the range specified in the present invention, high compression compactibility and good granulation properties can be demonstrated in a good balance.

The cellulose powder according to the present invention is prepared by hydrolyzing a natural cellulose substance under a condition where the acid concentration is lower than that in the conventional method. Namely, a natural cellulose substance is hydrolyzed for 40 to 110 minutes at the concentration of hydrochloric acid of 0.05 to 0.3% and the reaction temperature of 100 to 150° C. after the reaction temperature reaches to a predetermined reaction temperature. This hydrolysis can reduce impurities inside the cellulose particles correlated with the amount of organic carbon derived from the residual impurities extracted with hot water from the cellulose particles during the hydrolysis, and can increase the amount of organic carbon derived from the residual impurities in the cellulose particles after drying. A concentration of hydrochloric acid of 0.05% or more can provide a proper amount of organic carbon derived from residual impurities, which can enhance compactibility and disintegration properties in water, and attain a sharp particle size distribution of granules prepared by wet granulation. A concentration of hydrochloric acid of 0.3% or less is preferred because the amount of organic carbon derived from residual impurities is properly increased and a sharp particle size distribution of the cellulose particles is attained. A preferred range of the concentration of hydrochloric acid is 0.08 to 0.25%, particularly preferably 0.08 to 0.15%. A preferred range of the reaction temperature is 100 to 140° C.

Stirring should be performed under the hydrolysis condition to control the volume average particle size of particles in the cellulose dispersion liquid after the hydrolysis to be 70 to 150 μm. Preferably, after dehydration of the cellulose dispersion liquid, the product is washed with pure water several times, and is neutralized with an alkali, and then the product is again dehydrated to prepare a cellulose cake having 20 to 50% by weight of solid content.

Preferably, in the cellulose powder according to the present invention, the cellulose cake is mixed with pure water to prepare a cellulose slurry having 10 to 25% by weight of solid content. It is preferable that the cellulose slurry is stirred or the like to control the volume average particle size of the particles in the cellulose dispersion liquid before drying to be 40 μm or more and less than 50 μm, and then is spray dried. The particles in the cellulose dispersion liquid before drying having a volume average particle size of 40 μm or more are preferred because they improve the fluidity of the cellulose powder after drying. The particles in the cellulose dispersion liquid before drying having a volume average particle size of less than 50 μm are preferred because they barely demonstrate fibrous properties, and improve fluidity.

The rate of dry hot air during spray drying is preferably 11 to 40 m/s. Since a rate within this range prevents generation of fine powders and coarse particles during drying, and readily controls the sharpness of particle size distribution and the moisture retention rate within the ranges specified in the present invention, this range is preferable.

The spray drying temperature can be 150 to 300° C., which is an inlet temperature typically used.

Stirring during the reaction or a subsequent step can reduce the lengths of cellulose fibers. The volume average particle size of the particles can be reduced by a larger stirring force, and can be increased by a smaller stirring force. The stirring force can be properly adjusted so as to attain a desired volume average particle size to control the volume average particle size of the cellulose particle within the range specified in the present invention.

The stirring force can be adjusted by varying the size and shape of a stirring tank, the size and shape of a stirring blade, the number of rotations, the number of baffle plates, and the like.

After the reaction, the cellulose dispersion liquid is washed to adjust the pH. This obtained cellulose dispersion liquid before drying preferably has an electric conductivity (IC) of 200 μS/cm or less. When an IC of 200 μS/cm or less, the dispersibility of the particles in water and disintegration properties are improved. The IC is preferably 150 μS/cm or less, more preferably 100 μS/cm or less. The cellulose dispersion liquid can be prepared with water or water containing a small amount of an organic solvent in the range not to impair the effect of the present invention.

In the present invention, the natural cellulose substances indicate natural-derived vegetable fibrous substances containing cellulose such as wood materials, bamboo, cotton, and ramie, and preferably are substances having a crystal structure of cellulose I. From the viewpoint of yield in preparation, the natural cellulose substances are particularly preferably refined pulp products of these substances, which desirably contain 85% or more of a-cellulose.

The cellulose powder according to the present invention preferably has a moisture retention rate of 180 to 250%. In the present invention, the moisture retention rate is the maximum amount of water to be added (ml) to the cellulose powder (500 g), and is defined in terms of percentage to the solid content in the cellulose powder. The values of these properties are preferred because granules after granulation can have a sharp particle size distribution when the cellulose powder according to the present invention is used as an excipient for granulation. A sharper particle size distribution of the granules after granulation is preferred because capsule filling properties are higher and the drug content uniformity when the granules are compressed into a tablet is better.

In the present invention, the molded article indicates molded articles including the cellulose powder according to the present invention and properly prepared by a known method selected from mixing, stirring, granulation, pressing, size regulation, drying, and the like. Examples of molded articles used in pharmaceuticals include solid formulations such as tablets, powder medicines, subtle granules, granule agents, liquid extracts, pills, encapsulated formulations, lozenges, and poultices. The molded article according to the present invention includes not only those used in pharmaceuticals but also those used in foods such as confections, health foods, texture improvers, and dietary fiber strengthening agents, cake make-ups, bath agents, medicines for animals, diagnostic agents, pesticides, fertilizers, ceramic catalysts, and the like.

In the present invention, the molded article may comprise the cellulose powder according to the present invention in any content. The content is preferably 1 to 99.9% by weight based on the weight of the molded article. A content of 1% by weight or more can prevent abrasive wear or breakage of the molded article to give sufficient physical properties. The content is preferably 3% by weight or more, preferably 5% by weight or more. A content of 99.9% by weight or less attains a sufficient efficacy of an active ingredient. The content is preferably 90% by weight or less.

Furthermore, in the present invention, the molded article may contain, in addition to the cellulose powder according to the present invention, optionally other additives such as active ingredients, disintegrating agents, binders, fluidizing agents, lubricants, flavoring substances, fragrances, colorants, sweeteners, and surfactants.

Examples of the disintegrating agent include celluloses such as croscarmellose sodium, carmellose, carmellose calcium, carmellose sodium, and low substituted hydroxypropyl cellulose; starches such as carboxy methyl starch sodium, hydroxypropyl starch, rice starch, wheat starch, corn starch, potato starch, and partly pregelatinized starch; and crospovidone.

Examples of the binder include saccharides such as white sugar, glucose, lactose, and fructose; sugar alcohols such as mannitol, xylitol, maltitol, erythritol, and sorbitol; gelatin; water-soluble polysaccharides such as pullulan, carrageenan, locust bean gum, agar, glucomannan, xanthan gum, tamarind gum, pectin, alginic acid sodium, and gum arabic; celluloses such as microcrystalline cellulose, powder cellulose, hydroxypropyl cellulose, hydroxypropylmethyl cellulose, and methyl cellulose; starches such as pregelatinized starch and starch glue; synthetic polymers such as polyvinylpyrrolidone, carboxyvinyl polymer, and polyvinyl alcohol; and inorganic substances such as calcium hydrogenphosphate, calcium carbonate, synthetic hydrotalcite, and magnesium silicate aluminate.

Examples of the fluidizing agent include hydrous silicon dioxide and light anhydrous silicic acid. Examples of the lubricant include magnesium stearate, calcium stearate, stearic acid, sucrose fatty acid esters, and talc. Examples of the flavoring substances include glutamic acid, fumaric acid, succinic acid, citric acid, sodium citrate, tartaric acid, malic acid, ascorbic acid, sodium chloride, and 1-menthol.

Examples of the fragrances include oils such as orange, vanilla, strawberry, yogurt, menthol, fennel, cinnamon, picea, and peppermint oils; and green tea powder. Examples of the colorants include food dyes such as food dye red No. 3, food dye yellow No. 5, and food dye blue No. 1; sodium copper chlorophyllin, titanium oxide, and riboflavin. Examples of the sweeteners include aspartame, saccharin, dipotassium glycyrrhizinate, stevia, maltose, maltitol, mizuame, and powder of *Hydrangea macrophylla* var. thunbergii. Examples of the surfactants include phosphorus lipid, glycerol fatty acid esters, polyethylene glycol fatty acid esters, sorbitan fatty acid esters, and polyoxyethylene hardened castor oil.

In the present invention, the active ingredient indicates active pharmaceutical ingredients, pesticide ingredients, fertilizer ingredients, livestock food ingredients, food ingredients, cosmetic ingredients, dyes, fragrances, metals, ceramics, catalysts, surfactants, and the like, and may be in any form of powder, crystal, oil, and solution, for example. The active ingredient may be coated to control dissolution, reduce bitterness, and the like. The cellulose powder according to the present invention is particularly effective to the active ingredients having bad odors.

Examples of active pharmaceutical ingredients include Kampo medicines, crude drugs, and natural and synthetic pharmaceuticals orally administered and having bad odors, such as antipyretic analgesic antiphlogistics, hypnotics, anti-sleepiness drugs, antidizziness drugs, pediatric analgesics, stomachics, antacid, digestive drugs, cardiotonics, antiarrhythmic drugs, antihypertensives, vasodilators, diuretics, antiulcer drugs, intestinal regulators, antiosteoporosis drugs, antitussive expectorants, antiasthmatic drugs, antibacterial drugs, anti-pollakiuria drugs, analeptics, and vitamins. bb1

Examples of Kampo medicines include: ryokeikansoto, meiroinkakikuka, ryokeijutsukanto, ryokankyomishingen-into, ryutanshakanto, renjuin, ryokyojutsukanto, rikkunshito, rikkosan, ryokeimikanto, bushininjinto, mashiningan, makyoyokukanto, mokuboito, makyokansekito, maoto, maobushisaishinto, yohakusan, hontonto, hoyokangoto, yokuininto, hohaito, yokuibushihaisyosan, hochuekkito, yokukansan, yokukansankachimpihange, yokukansankasyakuyakuoren, hokikenchuto, heiisan, bunshoto, boiogito, boibukuryoto, huhiseimyakuto, bofutsushosan, bushikobeito, bukuryotakushato, bukuryoshigyakuto, bukuryokyoninkanzoto, hachigesan, hachimisenkiho, mibakujiogan, hangesyasinto, hangekobokuto, hangesankyuto, rokumigan, hatimijiogan, hangebyakujututenmato, bakumondoutou, byakujutusan, byakujutubusitou, hainoto, hainosan, hainosankyuto, byakkokaninjinto, byakkokakeisito, byakkoto, ninjinyoeito, bukuryukanto, busirityuto, ninjinto, bukuryoinkahange, bukuryoingohangekobokuto, bukuryoin, nyosinsan, teikiin, tibakujiogan, tikuyousekkoto, tyoyoto, toukakujokito, tennohosingan, tokisan, tudosan, tokisigyakukagosyuyusyokyoto, tokisigyakuto, tyoreitogosireito, tyoreito, tokisyakuyakusan, tokisyakuyakusankabusi, tokisyakuyakusankaninjin, tokisyakuyakusankaogityoto, tyotosan, tokito, tyokositeito, tokibaimokujinganryo, tyoijokito, dokkatsukiseito, tyuoko, dokkatuto, jizusoippo, nijututo, nitinto, jidabokuippo, daijokito, daisaikotokyodaio, daisaikoto, tyukentyuto, daikentyuto, daihangeto, daiobotanpito, daioubusito, daibouhuto, daiokanzoto, senkinkeimeisan, sankinnaitakusan, sensibyakujutusan, senkyutyatyosan, senkanmeimokuto, zokumeito, sessyoin, syozokumeito, seihaito, seinetuhoketuto, sokeikakketuto, seinetuhokito, sosikokito, seisinrensihin, sinbuto, sinpito, sinsentaituko, jinryobyakujututo, jingyobohuto, jingyokyokatuto, zensikunshito, jinsoin, shiniseihaito, seisituketanto, syoyosan(hatimisyoyosan), syohusan, seijokentsuto(kuhusyokutsuto), syobaito, seijobohuto, syomakakkonto, seisyoekkito, syohangekabukuryoto, syokyotoshinto, jasyosito, joganippou, syakosaito(sanmisyakosaito), juzentaihoto, jumihaidokuto, syakuyakukanzobushito, syakuyakukanzoto, juntyoto, syokentyuto, tokikentyuto, syakanzoto, syosaikoto, syosaikotokakikyosekko, seikiankaito, shiteito, syojokito, shichimotsukokato, tokiinshi, simotsuto, syoseiryuto, syoseiryutokasekko, syoseiryutokakyoninsekko, jijinmeimokuto, saisoin, saisyakurikkunshito, saikanto, sanmotsuougonto, sansouninto, jiinkokato, jiinshihoto, sanosyashinto, shiunko, satotsuko, shigyakuto, shigyakukaninjinto, shigyakusan, shikunshito, saireito, jiketsujunchoto, shikonboreito, saibokuto, shishishito, saikoseikanto, shishihakuhito, saikokeishito, jijintsujito, saikokeishikankyoto, kokikujiogan, kosharikkunshito, koshaheiisan, goshajinkigan, gokoto, shireito, goshuyuto, goreisan, gorinsan, takusyato, gomotsugedokusan, goshakusan, saikatsugekito, saikatsutokasenkyushini, goshitsusan, saikyohangeto, kososan, saikokaryukotsuboreito, kobokushokyohangeninjinkanzoto, saikosokanto, saikokikitsutokagomi, koshayoito, kishakunichinto, kigikenchyuto, keishakuchimoto, kyukikyogaito, kikyosekko, gedaishimotsuto, kenchutokeimakakuhanto, keimakakuhanto, keishikaogito, keishikakobokukyoninto, keishikakakkonto, keishito, keishikashakuyakushukyouninjinto, keishikashakuyakudaioto, keishikashakuyakuto, keikangan, keigairengyoto, keikyososooshinbuto, kumibinroto, kufugedokuto, keishikaryoujutsubuto, keishikajutsubuto, keishikaryukotsuboreito, kujinto, keishishakuyakuchimoto, gingyosan, kojito, keishibukurogankayokuinin, keishibukuryogan, gyokuheifusan, keihito, kyososan, keibohaidokusan, kyoseihatekigan, kanzobushito, kanzoshashinto, kanzokankyoto, kamiheisan, kamishoyosankasenkyujio, kamishimotsuto, kashokuyouhito, kairoto(san), kaikyusyokusyoto, kamishoyosan, kakkonkajutsubuto, kamigedokuto, dokkatsukakkonto, kakkontokasenkyushin'i, kakkontokakkonkokato, karogaihakuto, karogaihakuhakusyuto, kakkon'oren'ogonto, kankyoninjinhangegan, kakkoshokisan, ogikeishigomotsuto, ogikenchuto, ogikenchuto, kanzoto, kanbakutaisoto, kagenryokakusan, kanroinotsujitokyodaio, otsujito, orento, kikyoto, orengedokuto, kamikihito, kihito, oren'akyoto, kyukichoketsuindaiichikagen, kyukichoketsuin, oshosan, keishinieppiittokajutsuto, keishinieppiitto, keishieppito, chikujountanto, kanbakutaisoto, unpito, eppikajutsuto, untanto, unseiin, ureitsukisan, unkeito, uyakujunkisan, inchingoreisan, anchusankabukuryo, inchinkoto, eppikajutsubuto, ifuto, en'nenhangeto and anchusan and so on. These ingredients may be processed powders of raw powders or extract powders prepared by extracting raw powders, condensing the extracts, and drying the extracts.

Examples of crude drugs include fennel, corydalis tuber, scutellaria root, coptis rhizome, zedoary, glycyrrhiza, platycodon root, curcuma aromatica, schizonepeta spike, cinnamon bark, cyperus rhizome, magnolia bark, gardenia fruit, cornus fruit, dioscorea rhizome, rehmannia root, lithospermum, peony root, amomum seed, ginger, processed ginger, cnidium rhizome, atractylodes lancea rhizome, perilla herb, rhubarb, jujube, alisma tuber, clove, citrus unshiu peel, Japanese angelica root, eucommia bark, ginseng, mint, pinellia tuber, atractylodes rhizome, poria sclerotium, processed aconite root, saposhnikovia root and rhizome, moutan bark, oyster shell, ephedra herb, *Alpinia officinarum* Hance, forsythia fruit, and deer antler velvet. Examples of the ingredients contained in Bofutsushosan include ephedra herb (*Ephedra sinica* Stapf, *Ephedra intermedia* Schrenk et C. A. Meyer, *Ephedra equisetina* Bunge), glycyrrhiza (*Glycyrrhiza uralensis* Fischer, *Glycyrrhiza glabra* Linne), ginger (*Zingiber officinale* Roscoe), Schizonepeta spike (*Schizonepeta tenuifolia* Briquet), Forsythia fruit (*Forsythia suspense* Vahl, *Forsythia viridissima* Lindley), Japanese angelica root (*Angelica acutiloba* Kitagawa, *Angelica acutiloba* Kitagawa var. sugiyamae Hikino), peony root (*Paeonia lactiflora* Pallas), cnidium rhizome (*Cnidium officinale* Makino), gardenia fruit (*Gardenia jasminoides* Ellis), mint (*Mentha arvensis* Linne var. piperascens Malinvaud), saposhnikovia root and rhizome (*Saposhnikovia divaricata* Schischkin), rhubarb (*Rheum palmatum* Linne, *Rheum tanguticum* Maximowicz, *Rheum officinable* Baillon, *Rheum coreanum* Nakai, or interspecific hybrids thereof), atractylodes rhizome (*Atractylodes japonica* Koidzumi ex Kitamura, *Atractylodes ovata* De Candolle), platycodon root (*Platycodon grandiflorum* A. De Candolle), and scutellaria root (*Scutellariae baicalensis* Georgi). These ingredients may be processed powders of raw powders or extract powders prepared by extracting raw powders, condensing the extracts, and drying the extract.

The content of the active ingredient in the molded article according to the present invention is preferably 0.01 to 99% by weight based on the weight of the molded article. At a content of the active ingredient of 0.01% by weight or more, sufficient efficacy can be expected. At a content of 99% by weight or less, abrasive wear or breakage of the molded article can be prevented by a sufficient amount of an excipient to give satisfactory physical properties to the molded articles.

In the present invention, the tablet indicates a molded article including the cellulose powder according to the present invention and optional other additives, which can be prepared by one of a direct compression tableting method, a granule compression method, and wet granulation compression (extragranular addition of cellulose powder). Among these, tablets prepared by the direct compression tableting method are particularly preferred.

Among the molded articles according to the present invention, preferably the tablets, when the tablet contains one or more active ingredients and one or more additives selected from saccharides, sugar alcohols, starches, and disintegrating agents, compounding of the cellulose powder according to the present invention attains a molded article, preferably a tablet having a hardness of 50 to 200 N, a tensile strength of 0.1 to 12 MPa, a friability of 0 to 0.5%, a swelling rate of the diameter of the molded article, preferably the tablet in acetone of 0 to 3.3%, and a disintegration time of 20 minutes or less. The amount of the cellulose powder compounded with the molded article, preferably the tablet is preferably 5 to 90% by weight. An amount of compounding in the range of 5 to 90% by weight is preferred because physical properties described above are well-balanced.

The compounding of the cellulose powder according to the present application with a molded article, preferably a tablet can attain a molded article, preferably a tablet having a hardness, a tensile strength, and a friability in the ranges above, a swelling rate of the diameter of the molded article, preferably the tablet in acetone of 0 to 3.3%, and a disintegration time of 20 minutes or less. The swelling rate of the diameter of the molded article, preferably the tablet in acetone is preferably 0 to 3%, more preferably 0 to 2%. A swelling rate of the diameter of the molded article, preferably the tablet in acetone in the range of 0 to 3.3% is preferred because the hardness, the tensile strength, and the friability are well-balanced.

The swelling rate of the diameter of the molded article, preferably the tablet in acetone is defined by a rate of change in the diameter (mm) of the molded article (preferably the tablet) before and after the molded article (the tablet) is dipped in acetone (25° C.) for 60 seconds, and is calculated by the following expression:

swelling rate (%) of diameter of molded article (tablet)=[(diameter of molded article (tablet) after dipping in acetone)−(diameter of molded article (tablet) before dipping in acetone)/(diameter of molded article (tablet) before dipping in acetone)]×100

High compatibility of the cellulose powder according to the present invention results in a low swelling rate of the diameter of the molded article, preferably the tablet in acetone. A number of drugs have poor compactibility. If such a drug is contained in a molded article, preferably a tablet in a higher content, the physical properties of the drug are reflected. The resulting molded article (tablet) has low hardness and is readily worn. At this time, with a cellulose powder having insufficient compactibility, a molded article, preferably a tablet having a hardness of 50 N or more and a friability of 0.5% or less may not be attained. In contrast, use of the cellulose powder according to the present invention can give a hardness and friability suitable for practical use to the molded article, preferably the tablets. A preferred range of a drug contained in the molded article, preferably the tablet is 30 to 90% by mass, preferably 50 to 80% by mass. The content in the range of 30 to 90% by mass are preferred from the viewpoint of hardness and friability.

If the swelling rate of the diameter of the molded article, preferably the tablet in acetone is 0.3 to 3%, the resulting molded article, preferably the tablet can disintegrate and dissolve quickly. The disintegration time specified in the Pharmacopeia of Japan is 20 minutes or less, preferably 10 minutes or less, more preferably 1 minute or less, particularly preferably 30 seconds or less. The amount of total organic carbon derived from the residual impurities in the molded article residues or in the cellulose powder obtained through washing of the molded article, preferably the tablet with acetone, ethanol, pure water, and ethanol sequentially and extraction is preferably more than 0.07 and 0.25% or less. The amount in the range of more than 0.07 and 0.25% or less is preferred from the viewpoint of compactibility.

The amount of total organic carbon derived from the residual impurities in the molded article (preferably the tablet) residues is defined by the difference (%) between the amount of total organic carbon (TOC) in the molded article residues extracted from the molded article residues with pure water (80 mL) and the amount of TOC in the molded article residues extracted from the molded article residues with an aqueous solution of 1% sodium hydroxide (80 mL). When the molded article residues are cellulose powder, the molded article residues are sufficiently washed with pure water. For this reason, the amount of total organic carbon (%) during extraction with pure water in the molded article residues is close to zero, and the amount of total organic carbon derived from the residual impurities in the molded article residues is substantially equal to the amount of total organic carbon (%) during extraction with aqueous solution of 1% NaOH. When the amount of total organic carbon (%) during extraction with pure water is detected, removal of impurities by washing with pure water may be insufficient or removal of acetone and ethanol residuals by drying may be insufficient. For this reason, the amount of pure water used in extraction is increased 1.3 to 2 times, or the drying temperature is adjusted to 100 to 120° C. and the drying time is adjusted to 3 to 5 hr. The amount of total organic carbon derived from the residual impurities in the molded article residues obtained through washing of the molded article with acetone, ethanol, pure water, and ethanol sequentially and extraction can be checked by the following procedure.

i) 120 g of a molded article is placed in a 500 ml beaker, and 300 g of acetone is added. The mixture is stirred with a stirrer until molded article fragments disappear. The solution is vacuum filtered (with a Buchner funnel, and a filter paper for quantitative analysis, 5 C, diameter: 110 mm). When molded article fragments are found, the solution is subjected to ultrasonic treatment for 10 minutes, and is stirred for 30 minutes. This operation is repeated until the molded article fragments disappear.

ii) 100 mL of ethanol is added to the residues on the filter paper, is mixed with the residues with a spatula sufficiently, and is vacuum filtered (this operation is repeated 3 times). The ingredients barely soluble in water are removed by the operations i) and ii).

iii) The residues treated in ii) are added to 1000 mL of pure water, is stirred with a stirrer for 10 minutes, and is vacuum filtered.

iv) The residues treated in iii) are added to 600 ml of pure water, is stirred with a stirrer for 10 minutes, and is vacuum filtered.

v) The residues treated in iv) are added to 1000 mL of pure water, and the mixture is heated at 80 to 100° C. for 30 minutes while the mixture is stirred with a stirrer. After cooling to 20 to 30° C., 5 µg/L of α-amylase is added, is stirred at 37° C. for 30 minutes, and is vacuum filtered.

vi) 150 mL of ethanol is added to the residues treated in v). The residues are mixed with a spatula sufficiently, and is vacuum filtered (this operation is repeated 3 times). The water-soluble ingredients and starches are removed by the operations iii) to vi). The water-soluble ingredients include saccharides and sugar alcohols, and can be determined by a known method.

vii) The residues on the filter paper are scraped off therefrom, and are placed in a petri dish. The residues are dried at room temperature (20 to 30° C.) until a smell of ethanol disappears, and are dried at 100° C. for 3 hours to prepare a sample for measurement.

viii) About 2 g of the dried residues are placed in a cell for measurement, and are measured by near-infrared spectroscopy. Thus, an absorption spectrum is obtained (name of the apparatus: InfraAlyzer 500, manufacturer: BRAN+LUBBE). When the peaks indicating second derivative values are detected at 1692 nm in an NIR absorption spectrum, the cellulose powder content (C (%)) in the molded article residues is calculated by the following expression:

$$C(\%) = \text{intensity of NIR second derivative spectrum} \times 316583 + 95.588$$

When the peaks indicating the second derivative values in the NIR absorption spectrum are found at 1692 nm, crospovidone residues are contained in addition to the cellulose powder. The content of the cellulose powder in the dried residues is determined by the above expression. Instead of the molded article in (i), three composition powders of cellulose powder/crospovidone=100/0, 50/50, and 0/100 are prepared. Through the operations (i) to (vii), dried residues are each prepared. The intensities of the NIR second derivative spectrums are measured with the InfraAlyzer 500 (manufacturer: BRAN+LUBBE). From the three calibration curves, the coefficients in the above expression can be determined.

When no peaks of second derivative values in the NIR absorption spectrum are detected at 1692 nm, and the amount of total organic carbon (TOC) extracted with pure water (80 mL) from the dried residues in the dried residues is 0.0%, the dried residues are composed of only the cellulose powder. At an amount of TOC of more than 0.0%, disintegrating agents other than starch and crospovidone may be contained. To remove these, dried residues are dispersed in 50 mL of pure water, and are passed through a sieve having an opening of 10 µm to remove particles other than the cellulose powder. The filtrate is evaporated, and the resulting product is dried and solidified to prepare dried residues in ix). When the amount of total organic carbon (%) in the residues during extraction with pure water exceeds 0.0% even after this operation, the dried residues are dispersed in 50 mL of pure water (may be optionally subjected to ultrasonic and homogenizing treatments), and are centrifuged at 2000 G. The supernatant is evaporated, and the resulting product is dried and solidified to prepare dried residues in (ix).

ix) <Case where peaks of second derivative values in NIR absorption spectrum are detected at 1692 nm in viii)>

The dried residues (A (g), 4 to 4.5 g as a guideline) are weighed, and are added to 80 ml of 1% NaOH aqueous solution. The mixture is stirred with a stirrer for 5 minutes, and is vacuum filtered. The filtrate is extracted to measure the volume (X (mL)). The filtrate is acidified with hydrochloric acid (pH: 2 to 3). The amount of total organic carbon ($TOC_{1\%NaOH}$ (mg/L)) is measured with a total organic carbon analyzer (manufactured by SHIMADZU Corporation, TOC-VCSH, by a TC-IC method). Because the residues are sufficiently washed with pure water, the amount of total organic carbon (%) during extraction with pure water is considered as zero. Accordingly, the amount of organic carbon derived from the residual impurities in the cellulose powder contained in the residue is equal to the amount of total organic carbon (%) during extraction with aqueous solution of 1% NaOH. Calculation is performed as follows:

amount of cellulose powder residue (B(g)) in residue extracted from molded article=A×C/100 amount of total organic carbon (Y(mg)) in cellulose powder residue=($TOC_{1\% NaOH}$/1000)×X−0.4/100×(A−B)×1000

The coefficient 0.4 is the amount of total organic carbon (%) when 2.5 g of a crospovidone powder is used as the molded article in (i) to prepare dried residues through the treatments to (vii), and the dried residues are extracted with 80 ml of 1% NaOH aqueous solution.

amount of total organic carbon (%) derived from residual impurities in molded article residues obtained through washing of the molded article with acetone, ethanol, pure water, and ethanol sequentially and extraction=Y/(1000×B)×100=Y/(10×B) <Case where peaks of second derivative values in NIR absorption spectrum are not detected at 1692 nm in viii)>

The dried residues ($A_{H2O}$ (g): during extraction with pure water, $A_{1\% NaOH}$(g): during extraction with a 1% NaOH aqueous solution) are weighed, and 80 mL of pure water or 1% NaOH aqueous solution is added. The mixture is stirred in a beaker for 5 minutes (with a stirrer), and is vacuum filtered (with a filter paper for quantitative analysis, 5 C, diameter: 110 mm) to remove the dried residues and obtain a filtrate. After the volume of the total amount of the filtrate ($V_{H2O}$: total amount (mL) in use of pure water, $V_{1\% NaOH}$: total amount (mL) in use of 1% NaOH aqueous solution) is measured, the filtrate is acidified with hydrochloric acid (pH: 2 to 3), and the amount of total organic carbon (TOC (mg/L)) was measured with a total organic carbon analyzer (manufactured by SHIMADZU Corporation, TOC-VCSH, by a TC-IC method). The TOC in use of pure water is $TOC_{H2O}$, and the TOC in use of 1% NaOH aqueous solution is $TOC_{1\% NaOH}$. The amount of organic carbon derived from the residual impurities in the molded article residues is calculated by the following expressions:

amount of total organic carbon (%) derived from residual impurities in molded article residues=amount of total organic carbon (%) during extraction with aqueous solution of 1% NaOH−amount of total organic carbon (%) during extraction with pure water amount of total organic carbon (%) during extraction with aqueous solution of 1% NaOH:

$$= [(TOC_{1\% NaOH} \text{ (mg/L)}/1000) \times V_{1\% NaOH} \text{ (mL)}]/A_{1\% NaOH} \times 1000 \text{ (mg)} \times 100$$

amount of total organic carbon (%) during extraction with pure water:

=[($TOC_{H2O}$ (mg/L)/1000)×$V_{H2O}$ (mL)]/$A_{H2O}$×1000 (mg)×100

The cellulose powder according to the present invention can be used in wet granulation as a sugar-coating reinforcing agent in sugar-coated tablets, an extruding property improver in extrusion granulation, and granulation aids in crush granulation, fluidized bed granulation, high speed high shear granulation, tumbling granulation, and the like to prepare granule agents and granules for pressing. The granules for pressing can be prepared by dry granulation. Furthermore, tablets can be prepared by a method (wet granulation compression (extragranular addition of cellulose powder)) in which the cellulose powder according to the present invention is added to the granules for pressing prepared by such a known method, and the mixture is compressed. The cellulose powder according to the present invention can delay the granulation rate when active pharmaceutical ingredients having high moisture absorbing properties and high water solubility are granulated, so that generation of coarse particles are reduced to increase granulation yield. The cellulose powder according to the present invention, which has a low particle density, provides bulky granulated products. For this reason, the cellulose powder contributes to preparation of granules for pressing having high compression compactibility. The cellulose powder according to the present invention can be compounded with powder medicines to, for example, prevent blocking and improve fluidity, or can be compounded with encapsulated formulations to, for example, improve filling properties.

EXAMPLES

The present invention will now be described in more detail by way of Examples, but the scope of the present invention will not be limited to these. Physical properties in Examples and Comparative Examples were measured by the following methods.

1) Average degree of polymerization (-)

The average degree of polymerization is a value determined by a copper ethylene diamine solution viscosity method described in a microcrystalline cellulose check test(3) in the 15th edition of the Pharmacopeia of Japan.

2) Loss on drying (%)

1 g of a powder was dried at 105° C. for 3 hours, and the amount of weight reduction was expressed by weight percentage.

3) Volume average particle size (μm) of cellulose particle in cellulose dispersion liquid The particle size of particles in the cellulose dispersion liquid after hydrolysis or before drying was determined by the following procedure. A cellulose dispersion liquid was dropped onto a microscope stand. A glass slide was placed over the droplets. The droplets were dried, and an optical microscopic image was taken with a microscope. The optical microscopic image was subjected to image analysis processing (manufactured by Inter Quest Co., Ltd., apparatus: Hyper 700, software: Imagehyper). Among rectangles circumscribing a particle, the long side of the rectangle having the smallest area was determined, and the cumulative number 50% particle size was defined as the volume average particle size. At least 100 or more particles were subjected to image analysis processing.

4) Weight average particle size(μm) of cellulose powder

The weight average particle size of a powder sample was determined by sieving 10 g of the sample with a low tapping sieve shaker (sieve shaker type A manufactured by Heiko Seisakusho, Ltd.) and a JIS standard sieve (Z8801-1987) for 10 minutes to determine the particle size distribution. The particle size distribution was expressed as a cumulative weight 50% particle size.

5) Apparent specific volume ($cm^3/g$)

A powder sample was roughly placed in a 100 $cm^3$ glass measuring cylinder with a constant volume feeder or the like over 2 to 3 minutes. The top surface of the powder layer was leveled with a soft brush like an ink brush. The volume thereof was read, and was divided by the weight of the powder sample to determine the apparent specific volume. The weight of the powder was properly determined to have a volume of about 70 to 100 $cm^3$.

6) Apparent tapping density ($g/cm^3$)

With a commercially available powder physical property analyzer (manufactured by Hosokawa Micron Corporation, powder tester type PT-R), a powder was placed in a 100 $cm^3$ cup, and was tapped 180 times. The volume of the cup was divided by the weight of the powder layer remaining in the cup to determine the apparent tapping density.

7) Sharpness of particle size distribution

From the particle size distribution determined in 4), the integrated weight 10% particle size ($D_{10}$), the integrated weight 50 particle size ($D_{50}$), and the integrated weight 90% particle size ($D_{90}$) were determined, and the sharpness of particle size distribution was calculated by the following expression:

sharpness of particle size distribution =[($D_{50}/D_{10}$)+($D_{90}/D_{50}$)]/2

8) Amount of organic carbon (%) derived from residual impurities 80 mL of pure water or a 1% NaOH aqueous solution was added to a cellulose powder (W (mg), 5000 mg as a guideline), and was stirred for 10 minutes in a beaker (with a stirrer). Then, the cellulose powder was removed through vacuum filtration (with a filter paper for quantitative analysis, 5 C, diameter: 110 mm) to obtain a filtrate. The total volume (mL) of the filtrate was measured (where the total volume in use of water was $V_{H2O}$, and the total volume in use of 1% NaOH aqueous solution was $V_{1\%NaOH}$), and the filtrate was acidified with hydrochloric acid (pH: 2 to 3). Then, the amount of total organic carbon (TOC) was measured with a total organic carbon analyzer (manufactured by SHIMADZU Corporation, TOC-VCSH, by a TC-IC method). The TOC in use of pure water was $TOC_{H2O}$, and the TOC in use of 1% NaOH aqueous solution was $TOC_{1\%NaOH}$. The amount of organic carbon derived from the residual impurities was calculated by the following expressions:

amount of organic carbon (%) derived from residual impurities=amount of total organic carbon (%) during extraction with aqueous solution of 1% NaOH - amount of total organic carbon (%) during extraction with pure water amount of total organic carbon(%) during extraction with aqueous solution of 1% NaOH:

($TOC_{1\%\ NaOH}$(mg/L)×$V_{1\%NaOH}$(mL)/1000/$W$(mg))×100 amount of total organic carbon (%) during extraction with pure water:

($TOC_{H2O}$(mg/L)×$V_{H2O}$(mL)/1000/$W$(mg))×100

Figure 2A:
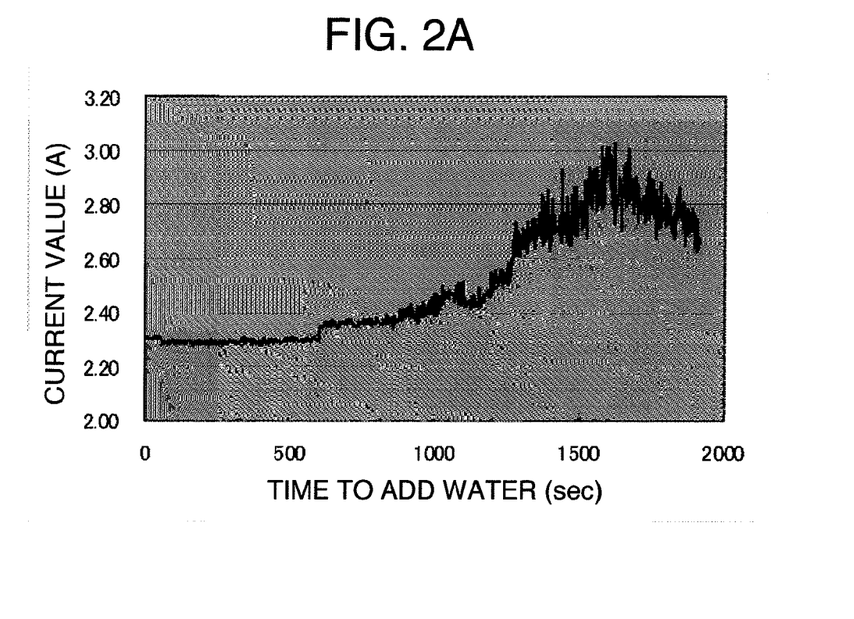
FIG. 2A is a graph in which the current consumed (ampere) is plotted every 2 seconds.
Figure 2B:
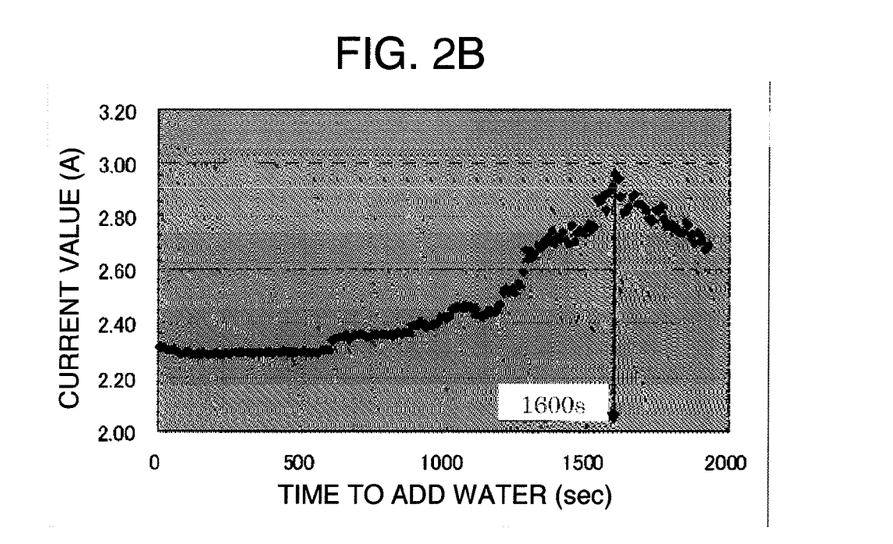
FIG. 2B is a graph in which the current consumed (ampere) is plotted against the moving average of five measured values.

9) Moisture retention rate (%) 500 g of a cellulose powder was placed in a container of a planetary mixer (versatile mixing stirrer 5DM-03-R, manufactured by DALTON CORPORATION), and a vinyl sheet was attached to the entire top surface of the container with an adhesive tape to prevent scattering of the powder. The vinyl sheet was partially cut, and a blade (beater type) was inserted from the cut. The container and blade were mounted on the planetary mixer, and stirring was started (63 rpm). Pure water at 20° C. was dropped with a tube pump (a hole was preliminarily made on an edge of the top surface of the container, and a tube was attached), and the time was measured at the same time when dropping of pure water was started. The amount of feed was adjusted to a targeted amount of 30 g/min. During stirring, with an ammeter (an AC power supply code was set in CLAMP ON SENSOR HIOKI 9272, and the signals were processed with CLAMP ON POWER Hi TESTER HIOKI 3165), the current consumed (ampere) was recorded every 2 seconds and the amount of dropped pure water was recorded every 2 minutes (FIG. 2A). The stirring rate was changed to 126 rpm after 10 minutes from the start of the dropping of pure water. The ampere increased as water was added. The moving average value (measured values: 5 values, interval: 10 seconds) was plotted (FIG. 2B) to determine the peak top, and the amount of water added (V) at the peak top was calculated. The amount of water added (V) was calculated by proportion from two amounts of water added measured at two points in the vicinity of the peak top. The moisture retention rate was calculated by the following expression:

moisture retention rate (%)=$V$(ml)/{500×(1—loss on drying)}(g)×100 loss on drying (%)=

(weight of cellulose powder before drying - weight of cellulose powder after drying at 105° C. for 3 hours) / weight of cellulose powder before drying For example, in FIG. 2B, the peak top is 1600 seconds (26 minutes 40 seconds). From the record, the amount of water added at 26 minutes is 789.7 g, and the amount of water added at 28 minutes is 850.0 g. From the average water adding rate between 26 minutes and 28 minutes (850.0−789.7)/2 =30.15 g/min, the amount of water added at 1600 seconds is determined as 789.7+30.15×(40/60)=809.8 g, namely, the amount of water added (V) is determined as 809.8 ml by calculation.

10) Angle of repose(°)

Using a Sugihara type repose angle measuring apparatus (slit size: depth: 10 mm, width: 50 mm, height: 140 mm, a protractor was disposed at a position of a width of 50 mm), the dynamic self-fluidity was measured when the cellulose powder was dropped into the slit with a constant volume feeder at a rate of 3 g/min. The angle formed by the bottom surface of the apparatus and the formed layer of the cellulose powder is an angle of repose.

11) Sharpness of particle size distribution of granules (−)

10 g of a sample was sieved for 10 minutes with a low tapping sieve shaker (sieve shaker type A manufactured by Heiko Seisakusho, Ltd.) and a JIS standard sieve (Z8801-1987) to measure the particle size distribution. The cumulative weight 10% particle size ($D_{10}$), the cumulative weight 50% particle size ($D_{50}$), and the cumulative weight 90% particle size ($D_{90}$) were calculated. The sharpness of particle size distribution of granules was determined from the following expression:

sharpness of particle size distribution of granules =($D_{50}$/$D_{10}$ +$D_{90}$/$D_{50}$)/2

The sharpness of particle size distribution of granules is preferably in the range of 1.0 to 3.0.

12) Variation in weight of tablet (CV) (%)

The weights of 20 tablets prepared by rotary press were measured. The average weight and the standard deviation of the weight were determined, and a coefficient of variation (%) defined by (standard deviation / average weight)×100 was determined to evaluate variation in the weight. A lower coefficient of variation indicates a small variation. The value suitable for practical use is 1.0% or less. A lower value is preferred, and a variation of 0.8% or less indicates that the weights of products are significantly stable.

13) Hardness (N)

Cylindrical molded articles or tablets were broken with a Schleuniger durometer (manufactured by Freund Corporation, type 6D) by applying a load in the diameter direction of the cylindrical molded article or the tablet, and the load at this time was measured. The hardness was expressed as the number average of five samples. A cylindrical molded article composed of 100% cellulose powder was prepared as follows. 0.5 g of a sample was placed in a die (manufactured by Kikusui Seisakusho Ltd., material SUK2, 3 was used), and was compressed at 10 MPa with a flat-surface punch (manufactured by Kikusui Seisakusho Ltd., material SUK2, 3 was used) having a diameter of 1.13 cm (bottom area: 1 $cm^2$). The stress was kept for 10 seconds to prepare a cylindrical molded article (a compressor manufactured by AIKOH ENGINEERING CO., LTD., PCM-1A was used, the compression rate was about 10 cm/min). The hardness suitable for practical use is 50 N or more in the tablet having a diameter of 8 mm and is 70 N or more in the tablet having a diameter of 9 mm or more.

14) Disintegration time (min)

A disintegration test was performed in accordance with a general test method and a tablet disintegration test method specified in the 15th edition of the Pharmacopeia of Japan. The disintegration time of a cylindrical molded article or a tablet in 37° C. pure water was determined with a disintegration tester (manufactured by TOYAMA SANGYO CO., LTD., type NT-40HS with a disk). The number average of six samples was determined. Tablets should be disintegrated within 30 minutes. Tablets were preserved in a glass air-tight bottle having a volume of 50 $cm^3$ for 6 months at 40° C. and 75% RH. The disintegration times before and after preservation were measured.

15) Friability of tablet (%)

The weights (Wa) of 20 tablets were measured. These tablets were placed in a tablet friability tester (PTFR-A, manufactured by Pharma Test Apparatebau AG), and were rotated at 25 rpm for 4 minutes. Then, fine powders adhering to the tablets were removed, and the weights (Wb) were again measured. The friability was calculated by the expression (7):

friability=100×($Wa-Wb$)/$Wa$

Tablets suitable for practical use should have a friability of 0.5% or less.

16) Tensile Strength (MPa)

The hardness of a tablet: H (N), the diameter of the tablet (the largest diameter was used in caplets or the like): D (mm), and the thickness of the tablet: T (mm) were determined, and the tensile strength was calculated by the following expression:

tensile strength(MPa)=2×$H$/(3.14×$D$×$T$)

17) Intraparticle Pore Volume ($cm^3$/g)

Pore distribution was determined with AutoPore, type 9520 (trade name) manufactured by SHIMADZU Corporation by mercury porosimetry. The sample powders used in the measurement were dried at room temperature for 15 hours under reduced pressure. From the pore distribution deteiniined in the measurement at an initial pressure of 20 kPa, the total volume of pores having a diameter of 0.1 to 15 μm was defined as the intraparticle pore volume.

Example 1

2 kg of a commercially available SP pulp (degree of polymerization: 1030, level-off degree of polymerization: 220) was shredded, and was added to 30 L of an aqueous solution of 0.05% hydrochloric acid. While the mixture was stirred (at a stirring rate of 234 rpm) with a low speed stirrer (manufactured by Ikebukuro Horo Kogyo Co., Ltd., 30 LGL reactor, blade diameter: about 30 cm), the pulp was hydrolyzed at 145° C. for 70 minutes. The resulting acid-insoluble residues were filtered with a suction funnel. The filtered residues were washed with 70 L of pure water 4 times, and were neutralized with aqueous ammonia. The residues were placed in a 90 L plastic bucket, and pure water was added. While the mixture was stirred (at a stirring rate of 500 rpm) with a three-one motor (manufactured by HEIDON, type BLh1200, 8 MIM, blade diameter: about 10 cm), a cellulose dispersion liquid having a concentration of 16% was prepared (pH: 7.8, IC: 55 μS/cm).

The cellulose dispersion liquid was spray dried (liquid feed rate: 6 L/hr, inlet temperature: 180 to 220° C., outlet temperature: 50 to 70° C., hot air rate: 11 m/s) to prepare Cellulose powder A (loss on drying: 3.8%). The physical properties of Cellulose powder A and the physical properties of a cylindrical molded article prepared by compressing 100% Cellulose powder A are shown in Table 1.

Example 2

2 kg of a commercially available SP pulp (degree of polymerization: 1030, level-off degree of polymerization: 200) was shredded, and was added to 30 L of an aqueous solution of 0.08% hydrochloric acid. While the mixture was stirred (at a stirring rate of 234 rpm) with a low speed stirrer (manufactured by Ikebukuro Horo Kogyo Co., Ltd., 30 LGL reactor, blade diameter: about 30 cm), the pulp was hydrolyzed at 140° C. for 110 minutes. The resulting acid-insoluble residues were filtered with a suction funnel. The filtered residues were washed with 70 L of pure water 4 times, and were neutralized with aqueous ammonia. The residues were placed in a 90 L plastic bucket, and pure water was added. While the mixture was stirred (at a stirring rate of 500 rpm) with a three-one motor (manufactured by HEIDON, type BLh1200, 8 M/M, blade diameter: about 10 cm), a cellulose dispersion liquid having a concentration of 18% was prepared (pH: 7.5, IC: 60 μS/cm).

The cellulose dispersion liquid was spray dried (liquid feed rate: 6 L/hr, inlet temperature: 180 to 220° C., outlet temperature: 50 to 70° C., hot air rate: 24 m/s) to prepare Cellulose powder B (loss on drying: 3.6%). The physical properties of Cellulose powder B and the physical properties of a cylindrical molded article prepared by compressing 100% Cellulose powder B are shown in Table 1.

Example 3

2 kg of a commercially available KP pulp (degree of polymerization: 1030, level-off degree of polymerization: 190) was shredded, and was added to 30 L of an aqueous solution of 0.10% hydrochloric acid. While the mixture was stirred (at a stirring rate of 234 rpm) with a low speed stirrer (manufactured by Ikebukuro Horo Kogyo Co., Ltd., 30 LGL reactor, blade diameter: about 30 cm), the pulp was hydrolyzed at 135° C. for 100 minutes. The resulting acid-insoluble residues were filtered with a suction funnel. The filtered residues were washed with 70 L of pure water 4 times, and were neutralized with aqueous ammonia. The residues were placed in a 90 L plastic bucket, and pure water was added. While the mixture was stirred (at a stirring rate of 500 rpm) with a three-one motor (manufactured by HEIDON, type BLh1200, 8 M/M, blade diameter: about 10 cm), a cellulose dispersion liquid having a concentration of 19% was prepared (pH: 7.5, IC: 50 μS/cm).

The cellulose dispersion liquid was spray dried (liquid feed rate: 6 L/hr, inlet temperature: 180 to 220° C., outlet temperature: 50 to 70° C., hot air rate: 32 m/s) to prepare Cellulose powder C (loss on drying: 3.3%). The physical properties of Cellulose powder C and the physical properties of a cylindrical molded article prepared by compressing 100% Cellulose powder C are shown in Table 1.

Example 4

2 kg of a commercially available KP pulp (degree of polymerization: 1030, level-off degree of polymerization: 130) was shredded, and was added to 30 L of an aqueous solution of 0.15% hydrochloric acid. While the mixture was stirred (at a stirring rate of 80 rpm) with a low speed stirrer (manufactured by Ikebukuro Horo Kogyo Co., Ltd., 30 LGL reactor, blade diameter: about 30 cm), the pulp was hydrolyzed at 110° C. for 105 minutes. The resulting acid-insoluble residues were filtered with a suction funnel. The filtered residues were washed with 70 L of pure water 4 times, and were neutralized with aqueous ammonia. The residues were placed in a 90 L plastic bucket, and pure water was added. While the mixture was stirred (at a stiffing rate of 500 rpm) with a three-one motor (manufactured by HEIDON, type BLh1200, 8 M/M, blade diameter: about 10 cm), a cellulose dispersion liquid having a concentration of 19% was prepared (pH: 7.5, IC: 65 μS/cm).

The cellulose dispersion liquid was spray dried (liquid feed rate: 6 L/hr, inlet temperature: 180 to 220° C., outlet temperature: 50 to 70° C., hot air rate: 40 m/s) to prepare Cellulose powder D (loss on drying: 3.0%). The physical properties of Cellulose powder D and the physical properties of a cylindrical molded article prepared by compressing 100% Cellulose powder D are shown in Table 1.

Figure 1:
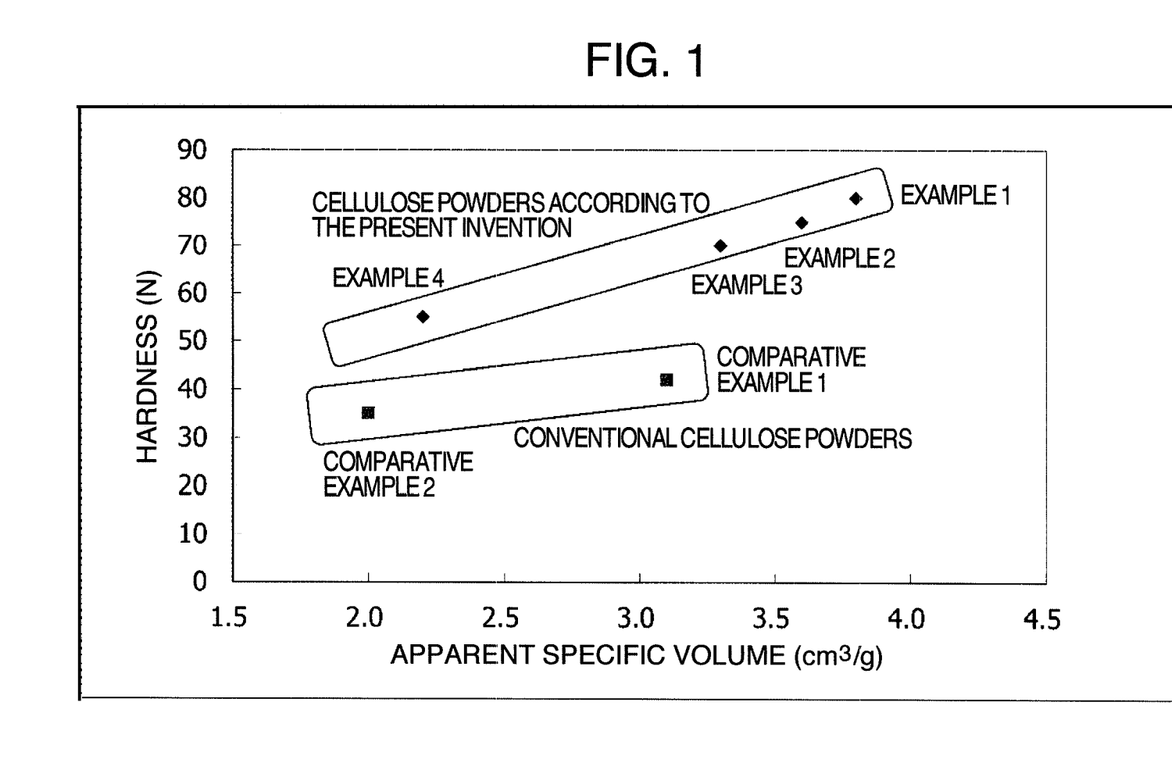
FIG. 1 is a diagram showing the relationship between the apparent specific volume and the hardness of the cellulose powder according to the present invention (Examples 1 to 4) and the conventional cellulose powder (Comparative Examples 1 and 2).

The cellulose powders according to the present application (Examples 1 to 4) have about 20 to 30% higher compactibility than that of the conventional cellulose powders even when the apparent specific volume is the same, as shown in FIG. 1 (Comparative Examples 1 and 2).

Example 5

Cellulose powder E was prepared by the same operation as in Example 1 except that the hydrolysis temperature was 100° C., and the concentration of the cellulose dispersion liquid was 8%.

The physical properties of Cellulose powder E and the physical properties of a cylindrical molded article prepared by compressing 100% Cellulose powder E are shown in Table 1.

Example 6

Cellulose powder F was prepared by the same operation as in Example 5 except that the concentration of hydrochloric acid was 0.28%, and the concentration of the cellulose dispersion liquid was 18%.

The physical properties of Cellulose powder F and the physical properties of a cylindrical molded article prepared by compressing 100% Cellulose powder F are shown in Table 1.

Example 7

Cellulose powder G was prepared by the same operation as in Example 3 except that the concentration of hydrochloric acid was 0.08%, and the hydrolysis time was 80 minutes.

The physical properties of Cellulose powder G and the physical properties of a cylindrical molded article prepared by compressing 100% Cellulose powder G are shown in Table 1.

Comparative Example 1

2 kg of a commercially available SP pulp (degree of polymerization: 1030, level-off degree of polymerization: 220) was shredded, and was hydrolyzed with 30 L of an aqueous solution of 0.14 N (0.49%) hydrochloric acid at 121° C. for 1 hour. The resulting acid-insoluble residues were filtered with a suction funnel. The filtered residues were washed with 70 L of pure water 4 times, and were neutralized with aqueous ammonia. The residues were placed in a 90 L plastic bucket. While the mixture was stirred with a three-one motor, a cellulose dispersion liquid having a concentration of 17% was prepared (pH: 6.4, IC: 64 µS/cm).

The cellulose dispersion liquid was spray dried (liquid feed rate: 6 L/hr, inlet temperature: 180 to 220° C., outlet temperature: 70° C., hot air rate: 30 m/s), and coarse particles were removed with a 325 mesh sieve to prepare Cellulose powder H (loss on drying: 4.1%, corresponding to Example 1 in JP 40-26274 B). The physical properties of Cellulose powder H and the physical properties of a cylindrical molded article prepared by compressing 100% Cellulose powder H are shown in Table 1.

Comparative Example 2

A commercially available KP pulp (degree of polymerization: 840, level-off degree of polymerization: 145) was hydrolyzed in an aqueous solution of 0.7% hydrochloric acid at 125° C. for 150 minutes. The hydrolyzed residues were neutralized, were washed, and were filtered to prepare a wet cake. The wet cake was sufficiently ground with a kneader. Ethanol was added in a volume ratio of ethanol to the wet cake of 1:1. The solution was compression filtered, and was dried with air. The dried powder was milled with a hammer mill, and coarse particles were removed with a 40 mesh sieve to prepare Cellulose powder I (dry weight: 3.0%, corresponding to Example 1 in JP 56-20471k). The physical properties of Cellulose powder I and the physical properties of a cylindrical molded article prepared by compressing 100% Cellulose powder I are shown in Table 1.

Comparative Example 3

Cellulose powder J was prepared by the same operation as in Example 3 except that the concentration of hydrochloric acid was 0.16%. The physical properties of Cellulose powder J and the physical properties of a cylindrical molded article prepared by compressing 100% Cellulose powder J are shown in Table 1.

Comparative Example 4

Cellulose powder K was prepared by the same operation as in Example 3 except that the hydrolysis time was 120 minutes. The physical properties of Cellulose powder K and the physical properties of a cylindrical molded article prepared by compressing 100% Cellulose powder K are shown in Table 1.

Comparative Example 5

Cellulose powder L was prepared by the same operation as in Example 3 except that the hydrolysis time was 60 minutes.

The physical properties of Cellulose powder L and the physical properties of a cylindrical molded article prepared by compressing 100% Cellulose powder L are shown in Table 1.

Comparative Example 6

Cellulose powder M was prepared by the same operation as in Example 3 except that the hydrolysis temperature was 90° C.

The physical properties of Cellulose powder M and the physical properties of a cylindrical molded article prepared by compressing 100% Cellulose powder M are shown in Table 1.

Comparative Example 7

Cellulose powder N was prepared by the same operation as in Example 3 except that the hydrolysis temperature was 160° C.

The physical properties of Cellulose powder N and the physical properties of a cylindrical molded article prepared by compressing 100% Cellulose powder N are shown in Table 1.

Comparative Example 8

Cellulose powder O was prepared by the same operation as in Example 3 except that the hydrolysis temperature was 90° C., and the hydrolysis time was 50 minutes. The physical properties of Cellulose powder O and the physical properties of a cylindrical molded article prepared by compressing 100% Cellulose powder O are shown in Table 1.

Comparative Example 9

Cellulose powder P was prepared by the same operation as in Example 1 except that the hydrolysis temperature was 25° C., and the hydrolysis time was 30 minutes. The physical properties of Cellulose powder P and the physical properties of a cylindrical molded article prepared by compressing 100% Cellulose powder P are shown in Table 1.

Comparative Example 10

Cellulose powder Q was prepared by the same operation as in Example 2 except that the concentration of hydrochloric acid was 0.50%, the hydrolysis temperature was 90° C., and the hydrolysis time was 35 minutes. The physical properties of Cellulose powder Q and the physical properties of a cylindrical molded article prepared by compressing 100% Cellulose powder Q are shown in Table 1.

TABLE 1

| | Cellulose powder | Reaction conditions | | | Physical properties of cellulose dipersion liquid | | Drying | Physical properties of cellulose powder | |
|---|---|---|---|---|---|---|---|---|---|
| | | Concentration of hydrochloric acid (%) | Hydrolysis temperature (° C.) | Hydrolysis time (min) | Volume average particle size (μm) after reaction | Volume average particle size (μm) before drying | conditions Hot air rate (m/s) | Average degree of polymerization (−) | Weight average particle size (μm) |
| Example | | | | | | | | | |
| 1 | A | 0.05 | 145 | 70 | 146 | 49 | 11 | 280 | 38 |
| 2 | B | 0.08 | 140 | 110 | 120 | 47 | 24 | 200 | 70 |
| 3 | C | 0.10 | 135 | 100 | 115 | 45 | 32 | 190 | 40 |
| 4 | D | 0.15 | 110 | 105 | 70 | 40 | 40 | 130 | 220 |
| 5 | E | 0.05 | 100 | 70 | 148 | 54 | 15 | 200 | 40 |
| 6 | F | 0.28 | 100 | 70 | 100 | 42 | 24 | 185 | 45 |
| 7 | G | 0.08 | 135 | 80 | 123 | 44 | 35 | 200 | 80 |
| Comparative Example | | | | | | | | | |
| 1 | H | 0.49 | 121 | 60 | 65 | 30 | 20 | 220 | 49 |
| 2 | I | 0.70 | 125 | 150 | 50 | 25 | 0.1 | 145 | 40 |
| 3 | J | 0.16 | 135 | 100 | 65 | 38 | 32 | 120 | 56 |
| 4 | K | 0.10 | 135 | 120 | 80 | 43 | 32 | 180 | 44 |
| 5 | L | 0.10 | 135 | 60 | 151 | 55 | 32 | 180 | 59 |
| 6 | M | 0.10 | 90 | 100 | 180 | 65 | 32 | 330 | 70 |
| 7 | N | 0.10 | 160 | 100 | 63 | 28 | 32 | 170 | 45 |
| 8 | O | 0.10 | 90 | 50 | 210 | 75 | 0.1 | 400 | 35 |
| 9 | P | 0.05 | 25 | 30 | 294 | 110 | 10 | 580 | 210 |
| 10 | Q | 0.50 | 90 | 35 | 170 | 75 | 0.1 | 360 | 90 |

| | Physical properties of cellulose powder | | | | | | | Cylindrical molded article composed of 100% cellulose powder Hardness (N) |
|---|---|---|---|---|---|---|---|---|
| | Apparent specific volume (cm3/g) | Tapping density (g/cm3) | Angle of repose (°) | Sharpness of particle size distribution (−) | Amount of organic carbon (%) derived from residual impurites | Intraparticle pore volume (cm3/g) | Moisture retention rate (%) | |
| Example | | | | | | | | |
| 1 | 3.8 | 0.35 | 40 | 2.4 | 0.145 | 0.25 | 250 | 80 |
| 2 | 3.6 | 0.48 | 37 | 2.5 | 0.131 | 0.21 | 230 | 75 |
| 3 | 3.3 | 0.53 | 40 | 1.8 | 0.116 | 0.20 | 200 | 70 |
| 4 | 2.2 | 0.6 | 38 | 2.7 | 0.090 | 0.12 | 180 | 55 |
| 5 | 13.0 | 0.21 | 56 | 2.0 | 0.250 | 0.15 | 300 | 100 |
| 6 | 3.4 | 0.55 | 45 | 2.3 | 0.160 | 0.19 | 210 | 70 |
| 7 | 4.5 | 0.35 | 38 | 2.6 | 0.248 | 0.21 | 245 | 85 |
| Comparative Example | | | | | | | | |
| 1 | 3.1 | 0.41 | 44 | 3.5 | 0.070 | 0.24 | 170 | 42 |
| 2 | 2.0 | 0.63 | 35 | 3.2 | 0.062 | 0.18 | 105 | 35 |
| 3 | 2.5 | 0.58 | 38 | 3.2 | 0.085 | 0.21 | 175 | 48 |
| 4 | 2.5 | 0.61 | 37 | 3.4 | 0.080 | 0.19 | 178 | 47 |
| 5 | 4.2 | 0.29 | 48 | 4.2 | 0.252 | 0.20 | 290 | 88 |
| 6 | 5.0 | 0.22 | 54 | 4.0 | 0.264 | 0.22 | 310 | 90 |
| 7 | 1.9 | 0.61 | 48 | 3.1 | 0.063 | 0.18 | 160 | 32 |
| 8 | 15.1 | 0.12 | 63 | 4.6 | 0.330 | 0.22 | 335 | 38 |
| 9 | 18.0 | 0.08 | 65 | 3.9 | 0.420 | 0.18 | 360 | 31 |
| 10 | 14.1 | 0.19 | 59 | 5.8 | 0.341 | 0.19 | 325 | 42 |

Example 8

1120 g of Bofutsushosan Extract-F (manufactured by Alps Pharmaceutical Industry Co., Ltd.), 400 g of Cellulose powder A, and 80 g of a pregelatinized starch "Swelstar" PD-1 (manufactured by Asahi Kasei Chemicals Corporation) were placed in a vertical granulator (VG-10, manufactured by Powrex Corporation). While the mixture was stirred (impeller: 280 rpm, cross screw: 3000 rpm), 200 g of an aqueous solution of 6% HPC-L was added, and the mixture was kneaded for 3 minutes to prepare granules prepared by granulation. After the granules prepared by granulation were dried, the granules were sieved with a 1410 μm sieve to prepare granules for pressing. 10 g of vegetable magnesium stearate (TAIHEI CHEMICAL INDUSTRIAL CO., LTD.) was added to 1000 g of the granules for pressing, and was mixed therewith in a plastic bag for 30 seconds. The mixture was pressed with a rotary presser ("Clean Press Correct 12HUK" (trade name), manufactured by Kikusui Seisakusho Ltd.) (compression force: 10 kN, weight: 380 mg, diameter: 9.5 mm, open feeder, the number of rotations of the turn table: 54 rpm). The physical properties of the resulting tablet are shown in Table 2.

Examples 9 to 15

The same operation was performed as in Example 5 except that the cellulose powder was changed to Cellulose powders B to G, and the amount of the aqueous solution of 6% HPC-L was changed to 180 g in Cellulose powder B, 170 g in Cellulose powder C, 120 g in Cellulose powder D, 240 g in Cellulose powder E, 170 g in Cellulose powder F, and 210 g in Cellulose powder G. The physical properties of the resulting tablet are shown in Table 2.

Comparative Examples 11 to 20

The same operation was performed as in Example 5 except that the cellulose powder was changed to Cellulose powders H to Q, and the amount of the aqueous solution of 6% HPC-L was changed to 170 g in Cellulose powder H, 120 g in Cellulose powder I, 120 g in Cellulose powder J, 120 g in Cellulose powder K, 200 g in Cellulose powder L, 220 g in Cellulose powder M, 120 g in Cellulose powder N, 270 g in Cellulose powder O, 330 g in Cellulose powder P, and 250 g in Cellulose powder Q. The physical properties of the resulting tablets are shown in Table 2.

good. The disintegration time was 20 minutes or less, which was improved more significantly than that of the Comparative Examples. The tablets were placed in a glass air-tight bottle having a volume of 50 cm$^3$, and were preserved at 40° C. and 75% RH for 6 months. The disintegration time of the cellulose powder according to the present application after 6 months barely changed while the disintegration times in the Comparative Examples were all longer than those before preservation.

INDUSTRIAL APPLICABILITY

The cellulose powder according to the present invention attains improved compression compactibility. In addition, the cellulose powder according to the present invention uniformly holds Kampo medicines, sticky ingredients, or the like during granulation thereof, can attain a sharp particle size distribution of the cellulose powder to attain a sharp particle size distribution of the resulting granules, contributes to reduction in the disintegration time, and can give stable disintegration properties over time.

The invention claimed is:
1. A cellulose powder having:
an average degree of polymerization of 100 to 350,
a weight average particle size of more than 30 μm and 250 μm or less,

TABLE 2

| | | Physical properties of granules | | | | Physical properties of tablet | | | | | | | |
|---|---|---|---|---|---|---|---|---|---|---|---|---|---|
| | Cellulose powder | Particle size of granules $D_{10}$ (μm) | Particle size of granules $D_{50}$ (μm) | Particle size of granules $D_{80}$ (μm) | Sharpness of particle size distribution of granules (—) | Tablet weight CV (%) | Hardness (N) | Tensile strength (MPa) | Disintegration time (min) | Disintegration time after preservation (min) | Friability (%) | Swelling rate of tablet diameter (%) | Amount of total organic carbon (%) derived from residual impurities in tablet residues |
| Example | | | | | | | | | | | | | |
| 8 | A | 115 | 305 | 780 | 2.60 | 0.49 | 101 | 1.46 | 19 | 19 | 0.21 | 1.70 | 0.144 |
| 9 | B | 122 | 337 | 855 | 2.65 | 0.40 | 92 | 1.32 | 15 | 16 | 0.30 | 1.90 | 0.131 |
| 10 | C | 120 | 344 | 758 | 2.54 | 0.30 | 82 | 1.18 | 14 | 13 | 0.35 | 2.00 | 0.115 |
| 11 | D | 110 | 325 | 790 | 2.69 | 0.40 | 71 | 1.02 | 18 | 17 | 0.49 | 2.70 | 0.090 |
| 12 | E | 100 | 230 | 760 | 2.80 | 0.78 | 124 | 1.80 | 20 | 20 | 0.12 | 0.87 | 0.250 |
| 13 | F | 118 | 310 | 840 | 2.63 | 0.43 | 75 | 1.08 | 14 | 17 | 0.45 | 2.43 | 0.161 |
| 14 | G | 90 | 180 | 560 | 2.66 | 0.54 | 102 | 1.48 | 13 | 15 | 0.15 | 1.57 | 0.247 |
| Comparative Example | | | | | | | | | | | | | |
| 11 | E | 75 | 303 | 1070 | 3.79 | 0.90 | 75 | 1.09 | 32 | 41 | 0.54 | 3.40 | 0.065 |
| 12 | F | 110 | 350 | 1290 | 3.43 | 0.80 | 43 | 0.62 | 28 | 33 | 0.80 | 3.40 | 0.062 |
| 13 | G | 125 | 370 | 1193 | 3.09 | 0.70 | 65 | 0.94 | 30 | 38 | 0.58 | 3.50 | 0.086 |
| 14 | H | 125 | 380 | 1210 | 3.11 | 0.70 | 60 | 0.87 | 29 | 40 | 0.57 | 3.40 | 0.090 |
| 15 | I | 49 | 260 | 910 | 4.40 | 1.20 | 115 | 1.66 | 38 | 54 | 0.09 | 3.40 | 0.255 |
| 16 | J | 45 | 195 | 810 | 4.24 | 1.10 | 136 | 1.96 | 42 | 48 | 0.06 | 3.60 | 0.263 |
| 17 | K | 138 | 340 | 1249 | 3.07 | 0.80 | 32 | 0.46 | 25 | 30 | 1.51 | 3.8 | 0.061 |
| 18 | O | 67 | 150 | 610 | 4.80 | 2.5 | 30 | 0.43 | 54 | 78 | 1.72 | 3.92 | 0.330 |
| 19 | P | 46 | 133 | 420 | 4.12 | 3.5 | 23 | 0.33 | 67 | 93 | 2.50 | 4.20 | 0.419 |
| 20 | Q | 55 | 143 | 550 | 5.10 | 6.2 | 35 | 0.50 | 48 | 63 | 3.30 | 3.90 | 0.343 |

The cellulose powder according to the present invention had a proper amount of moisture and a proper amount of organic carbon derived from the residual impurities, and thus had a sharp particle size distribution of granules. The sharpness of particle size distribution of granules specified in the present invention is preferably closer to 1.0. Only use of the cellulose powder according to the present application provided a sharpness of 3.0 or less. For this reason, the tablet weight CV value was 0.8% or less, and was significantly an apparent specific volume of 2 to less than 15 cm$^3$/g,
a sharpness of particle size distribution of 1.5 to 2.9, and
an angle of repose of 36° or more and less than 44°.

2. The cellulose powder according to claim 1, wherein the apparent specific volume is 2 to 6 cm$^3$/g.

3. The cellulose powder according to claim 1, wherein the apparent specific volume is 2 cm$^3$/g or more and less than 4 cm$^3$/g.

4. The cellulose powder according to claim 1, wherein an intraparticle pore volume is 0.1 cm$^3$/g or more and less than 0.265 cm$^3$/g.

5. The cellulose powder according to claim 1, wherein an amount of organic carbon derived from residual impurities is more than 0.07 and 0.25% or less, the amount of organic carbon derived from residual impurities being defined by an expression (amount of total organic carbon (%) during extraction with aqueous solution of 1% NaOH)−(amount of total organic carbon (%) during extraction with pure water).

6. The cellulose powder according to claim 1, wherein the sharpness of particle size distribution is 1.5 to less than or equal to 2.2.

7. The cellulose powder according to claim 1, wherein a moisture retention rate is 180 to 250%.

8. A molded article, comprising a cellulose powder according to any one of claims 1 to 7.

9. The molded article according to claim 8, wherein the molded article contains one or more active ingredients.

10. A method of preparing a cellulose powder, comprising:
    hydrolyzing a natural cellulose substance at a hydrochloric acid concentration of 0.05 to 0.3% at a hydrolysis temperature of 100 to 150° C. for a hydrolysis time of 40 to 110 minutes to control a volume average particle size of particles in a cellulose dispersion liquid after the hydrolysis to be 70 to 150 μm, and then
    spray drying the resulting dispersion liquid to prepare a cellulose powder having:
        an average degree of polymerization of 100 to 350,
        a weight average particle size of the cellulose powder of more than 30 μm and 250 μm or less,
        an apparent specific volume of 2 to 15 cm$^3$/g,
        a sharpness of particle size distribution of 1.5 to 2.9, and
        an angle of repose of 36° or more and less than 44°.

11. A molded article comprising:
    one or more active ingredients, one or more additives selected from saccharides, sugar alcohols, starches, and disintegrating agents, and a cellulose powder,
    wherein the molded article has a hardness of 50 to 200 N, a tensile strength of 0.1 to 12 MPa, a friability of 0 to 0.5%, a swelling rate of a diameter of the molded article in acetone of 0 to 3.3% or less, and a disintegration time of 20 minutes or less, and
    wherein the cellulose powder has:
        an average degree of polymerization of 100 to 350,
        a weight average particle size of more than 30 μm and 250 μm or less,
        an apparent specific volume of 2 to less than 15 cm$^3$/g,
        a sharpness of particle size distribution of 1.5 to 2.9, and
        an angle of repose of 36° or more and less than 44°.

12. The molded article according to claim 11, comprising 5 to 90% by weight of the cellulose powder.

13. The molded article according to claim 11 or 12, wherein an amount of total organic carbon derived from residual impurities in molded article residues obtained through washing of the molded article with acetone, ethanol, pure water, and ethanol sequentially and extraction is more than 0.07 and 0.25% or less.

14. The molded article according to claim 11 or 12, wherein an amount of total organic carbon derived from residual impurities in the cellulose powder obtained through washing of the molded article with acetone, ethanol, pure water, and ethanol sequentially and extraction is more than 0.07 and 0.25% or less.

* * * * *